US009848881B2

(12) United States Patent
Sutton et al.

(10) Patent No.: US 9,848,881 B2
(45) Date of Patent: Dec. 26, 2017

(54) CLOT REMOVAL DEVICE FOR DEEP VEIN THROMBOSIS

(71) Applicant: Fusion Medical, Inc., Plymouth, MN (US)

(72) Inventors: Gregg Stuart Sutton, Maple Grove, MN (US); Eric Joseph Dille, Eden Prairie, MN (US); Jeffery Foster Larson, Dayton, MN (US)

(73) Assignee: Fusion Medical, Inc., Plymouth, MN (US)

( * ) Notice: Subject to any disclaimer, the term of this patent is extended or adjusted under 35 U.S.C. 154(b) by 283 days.

(21) Appl. No.: 13/890,892

(22) Filed: May 9, 2013

(65) Prior Publication Data
US 2014/0094841 A1    Apr. 3, 2014

Related U.S. Application Data

(60) Provisional application No. 61/644,796, filed on May 9, 2012.

(51) Int. Cl.
| | |
|---|---|
| *A61F 2/06* | (2013.01) |
| *A61B 17/12* | (2006.01) |
| *A61B 17/221* | (2006.01) |
| *A61B 17/3207* | (2006.01) |
| *A61B 17/22* | (2006.01) |

(52) U.S. Cl.
CPC ...... *A61B 17/12109* (2013.01); *A61B 17/221* (2013.01); *A61B 17/320725* (2013.01); *A61B 17/320758* (2013.01); *A61B 17/12045* (2013.01); *A61B 2017/22054* (2013.01)

(58) Field of Classification Search
CPC ........ A61B 17/3207; A61B 17/320725; A61B 17/320758; A61B 2017/320775
See application file for complete search history.

(56) References Cited

U.S. PATENT DOCUMENTS

| | | | |
|---|---|---|---|
| 5,766,191 A | 6/1998 | Trerotola | |
| 5,843,103 A * | 12/1998 | Wulfman | ....... A61B 17/320758 |
| | | | 606/159 |
| 6,652,548 B2 | 11/2003 | Evans et al. | |
| 6,660,014 B2 | 12/2003 | Demarais et al. | |
| 6,740,191 B2 * | 5/2004 | Clarke | .............. A61M 25/1034 |
| | | | 156/272.8 |
| 6,824,551 B2 | 11/2004 | Trerotola | |
| 7,108,704 B2 | 9/2006 | Trerotola | |
| 7,524,319 B2 | 4/2009 | Dubrul | |
| 8,057,496 B2 | 11/2011 | Fischer | |
| 2005/0124931 A1 | 6/2005 | Fulton et al. | |
| 2012/0143129 A1* | 6/2012 | Simpson | ........... B29C 66/73713 |
| | | | 604/96.01 |
| 2017/0020556 A1 | 1/2017 | Sutton et al. | |

\* cited by examiner

*Primary Examiner* — Ashley Fishback
(74) *Attorney, Agent, or Firm* — Stoel Rives LLP

(57) ABSTRACT

The invention being disclosed describes a medical device for removal of a thrombus or clot in a vascular setting by using a rotational, expandable basket structure in combination with drug infusion, blood/particle aspiration and clot isolation by distal and proximal occlusion.

20 Claims, 3 Drawing Sheets

CLOT REMOVAL DEVICE FOR DEEP VEIN THROMBOSIS

This application claims the benefit of U.S. Provisional Application No. 61/644,796, filed May 9, 2012, the contents of which are herein incorporated by reference.

BACKGROUND OF THE INVENTION

The fields of interventional radiology and cardiology require the removal of clot in an artery or vein to reduce the possibility of embolisms and vascular occlusions. Particularly, in the case of deep vein thrombosis (DVT), a disease state in which a patient presents with a blood clot in a peripheral vein, the clot must be removed so that it does not embolize and cause a pulmonary artery occlusion which is usually fatal. These clots are typically removed with pharmacological or mechanical means. For instance urokinase, a lytic agent can be injected to the site of the clot to cause dissolution. Or mechanical removal is attemped with aspiration catheters or, alternatively catheter based baskets or other mechanical maceration means are employed.

The limitation of these devices include non-control of mobile clots during removal, systemic risks of lytic agents, and vein or arterial damage due to mechanical removal devices. Therefore, a need exists for an improved clot removal device for deep vein thrombosis

INVENTION DESCRIPTION

It is the purpose of this invention to describe an improved device for removing clot in an artery or vein. The device of this invention comprises a catheter based mechanism with a rotating basket structure in combination with aspiration means as well as distal and proximal clot isolation means.

The rotating basket structure comprises a metallic or polymeric struts in a spiral or straight configuration. The basket structure is, for example, expandable in diameter from catheter diameter (or less) to a much larger diameter, such as 10-20 mm. Diameter is typically independently controlled in a proximal handle mechanism. The diameter expansion control is independent of rotational speed. The rotational speed of the basket is controlled with the proximal handle means at speeds ranging from, for example 500-5000 rpm, and is driven by a DC motor integral to the handle means. The basket structure can be made of strut material that provides enough stiffness to macerate and emulsify clots but conformable enough to ride over and not damage venous or arterial structures such as valves.

Another embodiment of the basket structure provides 2 or 3 separate and independent basket structures that can be independently expanded or contracted.

Yet another embodiment of the invention provides a bi-modal basket shape which optimizes the function of the device when passed through venous or arterial valves.

The occlusive isolation element of the invention comprises distal and proximal occlusion elements that function by inflation or by mechanical expansion. The occlusion elements provide isolation of the clot during maceration and infusion/aspiration so as to inhibit particle embolization and maintenance of lytic concentrations.

The infusion/aspiration means element the invention comprises a distal to proximal lumen in the outer part of the catheter shaft. The lumen terminates within the occlusive isolation zone with an opening optimized for vacuum. The vacuum is provided proximally in the handle mechanism via a vacuum syringe or vacuum pump.

The above summary of the present invention is not intended to describe each discussed embodiment of the present invention. This is the purpose of the figures and the detailed description that follows.

DRAWINGS

The invention may be more completely understood in connection with the following drawings, in which.

Figure 1:
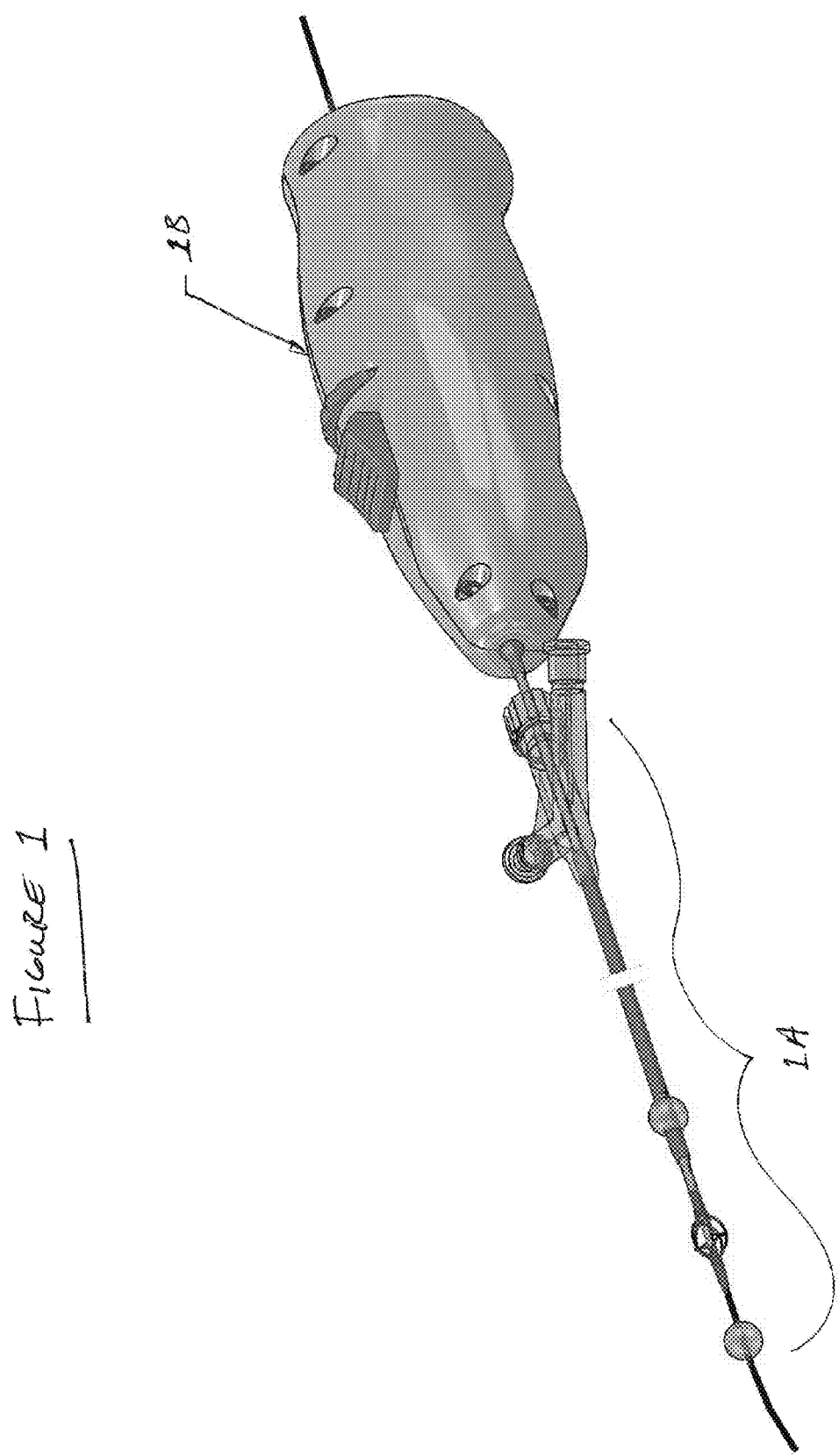
FIG. 1 shows the device in it's entirely from delivery/catheter portion (1A) to proximal control handle (1B).
Figure 2:
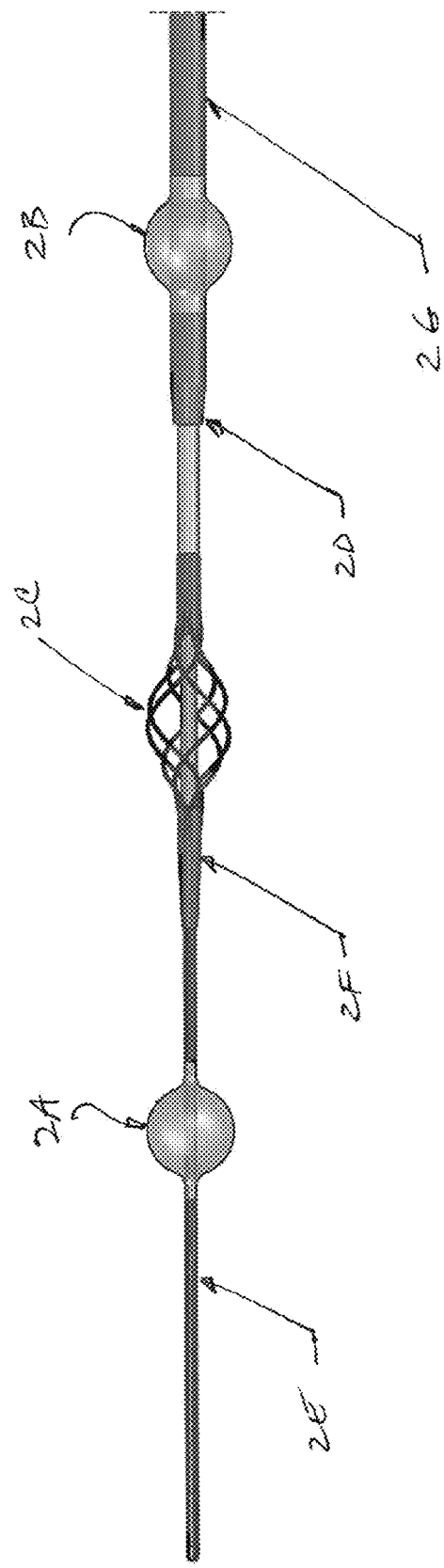
FIG. 2 shows the working end, or distal end of the device. Elements 2A and 2B are the occlusive balloon means. 2C shows the basket in the mid-expansion state. 2D is the infusion/aspiration port. 2E is the guidewire member portion of the device, 2F is the rotational member of the device and 2G is the infusion/aspiration outer sheath member of the device.
Figure 3:
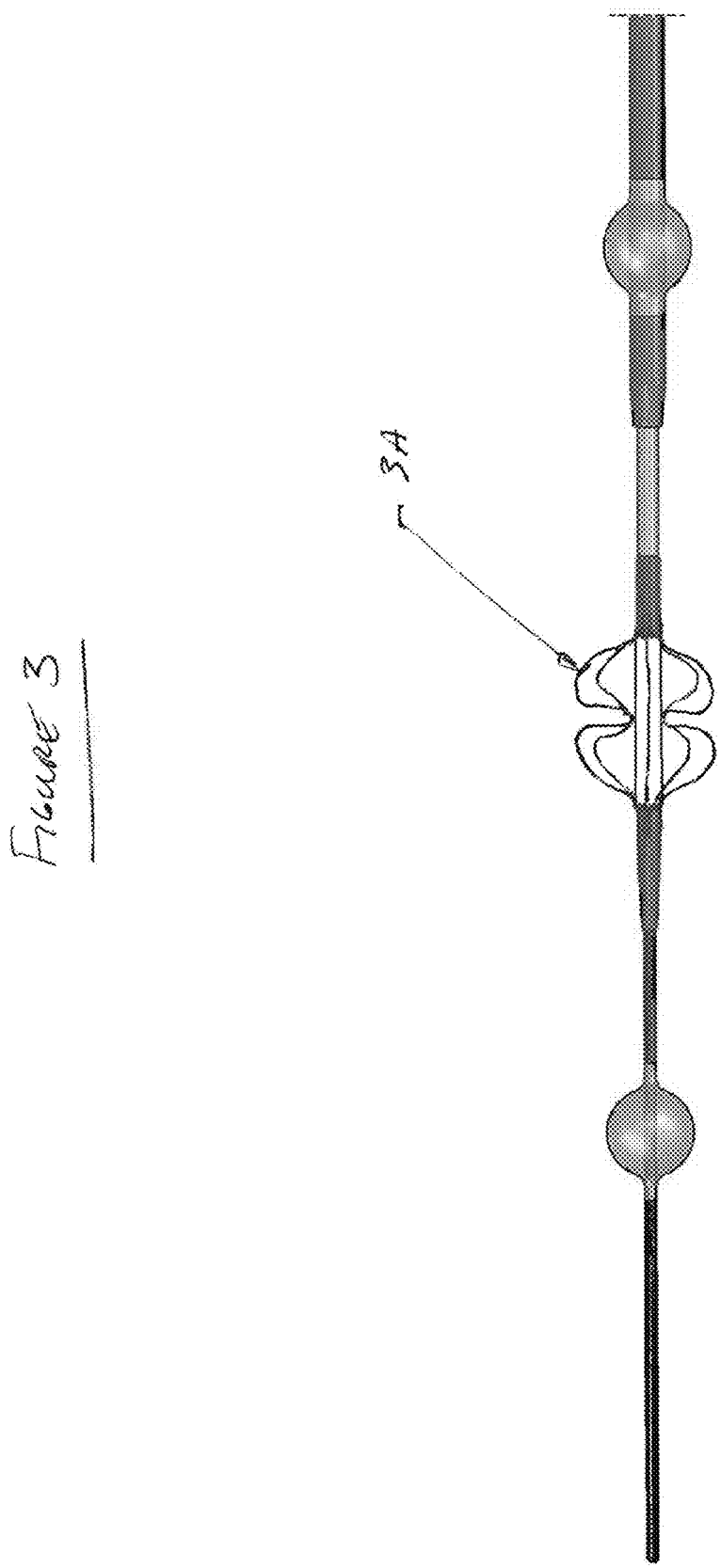
FIG. 3 shows another embodiment of the device which exhibits an axially bi-modal basket design (3A).

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

The present invention is directed to a medical device for removing thrombus or clot from the vasculature comprising, in an example embodiment, a distal occlusive element mounted on an inner guidewire member. A catheter member may be slideable over the guidewire member that has a distal clot macerating basket structure that is diametrally expandable. A basket structure can contain a plurality of struts to form an expanded elliptical shape or bi-modal elliptical shape. The catheter member and basket are rotatable at (500-10,000) rpm and controlled at a proximal handle member.

In some implementations the devices includes an outer infusion/aspiration catheter sheath that is slideable over the rotational catheter member and contains a proximal occlusion member and is operably connected to the proximal control handle. A proximal control handle that provides rotational speed control, basket expansion/contraction and infusion/aspiration fluid inputs may be included. The proximal control handle comprising an internal DC motor, gearing/belt system and through lumen access. The thrombus or clot removing device can be arranged such that occlusive isolation, basket rotation (clot maceration) and infusion/aspiration are operating simultaneously or in combination.

While the present invention has been described with reference to several particular implementations, those skilled in the art will recognize that many changes may be made hereto without departing from the spirit and scope of the present invention.

We claim:

1. A catheter for blockage removal for a circulatory system, comprising:
    a main tubular shaft comprising a distal tip and a control handle coupled to the proximal end of the main tubular shaft;

an isolation element coupled to the main tubular shaft, the isolation element comprising a first expandable isolation member and a second expandable isolation member; and a rotational member coupled to the main tubular shaft, the rotational member comprising a bi-modal expandable macerating element, wherein the rotational member is disposed between the first expandable isolation member and the second expandable isolation member, such that the diameter and speed of the rotational member is adjustable during removal of a blockage in the circulatory system.

2. The catheter according to claim 1, further comprising: an aspiration port along the main tubular shaft.

3. The catheter according to claim 2, wherein the aspiration port is located between the first expandable isolation member and the second expandable isolation member.

4. The catheter according to claim 1, wherein the first expandable isolation member and the second expandable isolation member are inflatable.

5. The catheter according to claim 1, wherein the bi-modal expandable macerating element comprises at least two struts.

6. The catheter according to claim 1, wherein the rotational member is configured to rotate at least 500 rpms.

7. A catheter for blockage removal for a circulatory system, comprising:
a main tubular shaft comprising a distal tip and a control handle coupled to the proximal end of the main tubular shaft;
an isolation element coupled to the main tubular shaft, the isolation element comprising a first expandable isolation member and a second expandable isolation member;
a rotational member coupled to the main tubular shaft, the rotational member comprising a bi-modal expandable macerating element; and
an aspiration port disposed along the main tubular shaft between the first expandable isolation member and the second expandable isolation member.

8. The catheter according to claim 7, wherein the rotational member is disposed between the first expandable isolation member and the second expandable isolation member.

9. The catheter according to claim 7, wherein the first expandable isolation member and the second expandable isolation member are inflatable.

10. The catheter according to claim 7, wherein the bi-modal expandable macerating element comprises struts.

11. The catheter according to claim 7, wherein the bi-modal expandable macerating element comprises at least two struts.

12. The catheter according to claim 7, wherein the rotational member is configured to rotate at least 500 rpms.

13. The catheter according to claim 7, wherein the expandable macerating elements are expandable independent of rotational speed.

14. The catheter according to claim 7, wherein the bi-modal expandable macerating element comprises first and second expandable macerating elements, wherein the first expandable macerating element is coupled to the main tubular shaft independent of the second expandable macerating element.

15. A method for removing a blockage, comprising:
inserting a catheter into a patient's circulatory system, wherein the catheter comprises a first expandable isolation member, a second expandable isolation member and a rotational member, wherein the rotational member includes an expandable macerating element;
expanding the first expandable isolation member and the second expandable isolation member;
expanding the expandable macerating element; and
rotating the expandable macerating element at least 500 rpms to macerate a clot,
wherein the rotational member diameter is expandable independent of rotational speed.

16. The method according to claim 15, further comprising:
aspirating the macerated clot from between the first expandable isolation member and the second expandable isolation member.

17. The method according to claim 15, further comprising:
collapsing the first expandable isolation member and the second expandable isolation member.

18. The method according to claim 17, further comprising:
removing the catheter from the patient's circulatory system.

19. The method according to claim 15, wherein the expandable macerating element comprises a bi-modal expandable macerating element.

20. The method according to claim 15, wherein the expandable macerating element comprises a first expandable macerating element and a second expandable macerating element.

* * * * *